United States Patent
Yonekura et al.

(10) Patent No.: US 9,593,343 B2
(45) Date of Patent: Mar. 14, 2017

(54) PLANT VARIANT, METHOD FOR PRODUCING PLANT VARIANT, AND METHOD FOR ACCUMULATING SOLUBLE SUGAR

(75) Inventors: Madoka Yonekura, Toyota (JP); Naohiro Aoki, Bunkyo-ku (JP); Ryu Ohsugi, Bunkyo-ku (JP); Masaki Okamura, Bunkyo-ku (JP); Tatsuro Hirose, Joetsu (JP); Chikara Ohto, Toyota (JP); Akio Miyao, Moriya (JP)

(73) Assignees: TOYOTA JIDOSHA KABUSHIKI KAISHA, Aichi-ken (JP); THE UNIVERSITY OF TOKYO, Tokyo (JP); INCORPORATED ADMINISTRATIVE AGENCY NATIONAL AGRICULTURE AND FOOD RESEARCH ORGANIZATION, Tsukuba-Shi (JP); NATIONAL INSTITUTE OF AGROBIOLOGICAL SCIENCES, Tsukuba-Shi (JP)

( * ) Notice: Subject to any disclaimer, the term of this patent is extended or adjusted under 35 U.S.C. 154(b) by 41 days.

(21) Appl. No.: 14/005,724

(22) PCT Filed: Mar. 22, 2012

(86) PCT No.: PCT/JP2012/001985
§ 371 (c)(1),
(2), (4) Date: Sep. 17, 2013

(87) PCT Pub. No.: WO2012/132348
PCT Pub. Date: Oct. 4, 2012

(65) Prior Publication Data
US 2014/0090107 A1 Mar. 27, 2014

(30) Foreign Application Priority Data
Mar. 28, 2011 (JP) ................. 2011-070763

(51) Int. Cl.
C12N 15/82 (2006.01)
C12N 9/10 (2006.01)
C12N 9/12 (2006.01)

(52) U.S. Cl.
CPC ....... C12N 15/8246 (2013.01); C12N 9/1051 (2013.01); C12N 9/1241 (2013.01); C12N 15/8245 (2013.01); C12Y 207/07027 (2013.01)

(58) Field of Classification Search
None
See application file for complete search history.

(56) References Cited

U.S. PATENT DOCUMENTS 5,498,831 A * 3/1996 Burgess et al. ............... 800/284
7,193,130 B2 3/2007 Tomes et al.
2003/0177533 A1 9/2003 Hannah et al.

FOREIGN PATENT DOCUMENTS

EP 1 461 431 B1 4/2010

OTHER PUBLICATIONS

Rösti et al, 2007, Functional Plant Bio., 34:480-489.*
Lee et al, 2007, Plant Mol. Bio., 65:531-546.*
Tian et al, 2009, PNAS, 106:21760-21765.*
Rolletschek et al, 2002, Planta, 214:954-964.*
Sandrine Rösti, et al., "A mutant of rice lacking the leaf large subunit of ADP-glucose pyrophosphorylase has drastically reduced leaf starch content but grows normally", Functional Plant Biology, 2007, pp. 480-489, vol. 34.
Jung-Il Park, et al., "Modification of sugar composition in strawberry fruit by antisense suppression of an ADP-glucose pyrophosphorylase", Molecular Breeding, 2006, pp. 269-279, vol. 17.
Hans Weber, et al., "Antisense-inhibition of ADP-glucose pyrophosphorylase in developing seeds of *Vicia narbonensis* moderately decreases starch but increases protein content and affects seed maturation", The Plant Journal, 2000, pp. 33-43, vol. 24, No. 1.
Bernd Müller-Röber, et al., "Inhibition of the ADP-glucose pyrophosphorylase in transgenic potatoes leads to sugar-storing tubers and influences tuber formation and expression of tuber storage protein genes", The EMBO Journal, 1992, pp. 1229-1238, vol. 11, No. 4.
Sang-Kyu Lee, et al., "Identification of the ADP-glucose pyrophosphorylase isoforms essential for starch synthesis in the leaf and seed endosperm of rice (*Oryza sativa* L.)", Plant Mol. Biol. 2007, pp. 531-546, vol. 65.
Takashi Akihiro, et al., "Gene Expression of ADP-glucose Pyrophosphorylase and Starch Contents in Rice Cultured Cells are Cooperatively Regulated by Sucrose and ABA", Plant Cell Physiology, 2005, pp. 937-946, vol. 46, No. 6.
Kamol Lertrat, et al., "Breeding for Increased Sweetness in Sweet Corn", International Journal of Plant Breeding, Feb. 28, 2007, pp. 27-30, vol. 1, No. 1.
Alison M. Smith, et al., "Evidence that the *rb* Locus Alters the Starch Content of Developing Pea Embryos through an Effect on ADP Glucose Pyrophosphorylase", Plant Physiol., 1989, pp. 1279-1284, vol. 89.
Tsan-Piao Lin, et al., "Isolation and Characterization of a Starchless Mutant of *Arabidopsis thaliana* (L.) Heynh Lacking ADPglucose Pyrophosphorylase Activity", Plant Physiol. 1988, pp. 1131-1135, vol. 86.
Tsan-Piao Lin, et al., "A Starch Deficient Mutant of *Arabidopsis thaliana* with Low ADPglucose Pyrophosphorylase Activity Lacks One of the Two Subunits of the Enzyme", Plant Physiol., 1988, pp. 1175-1181, vol. 88.

(Continued)

*Primary Examiner* — Jason Deveau Rosen
(74) *Attorney, Agent, or Firm* — Sughrue Mion, PLLC (57) ABSTRACT

This invention is intended to allow accumulation of large quantities of soluble sugars in tissue other than plant seeds. A plant is modified so as to suppress a gene encoding a subunit exhibiting the highest sequence similarity with the subunit encoded by the AGPL1 gene of rice among subunits constituting.

3 Claims, 1 Drawing Sheet (56) References Cited

OTHER PUBLICATIONS

Yasuko S. Nagai, et al., "Control of Starch Synthesis in Cereals: Metabolite Analysis of Transgenic Rice Expressing an Up-Regulated Cytoplasmic ADP-Glucose Pyrophosphorylase in Developing Seeds", Plant Cell Physiol., 2009, 635-643, vol. 50, No. 3.

Hikaru Satoh, et al., "Isolation and Characterization of Starch Mutants in Rice", J. Appl. Glycosci, 2003, pp. 225-230, vol. 50.

NF3982 line, "Rice Tos17 Insertion Mutant Database," retrieved online on Mar. 24, 2016, from https://tos.nias.affrc.go.jp/.

* cited by examiner

PLANT VARIANT, METHOD FOR PRODUCING PLANT VARIANT, AND METHOD FOR ACCUMULATING SOLUBLE SUGAR

CROSS REFERENCE TO RELATED APPLICATIONS

This application is a National Stage of International Application No. PCT/JP2012/001985 filed Mar. 22, 2012, claiming priority based on Japanese Patent Application No. 2011-070763 filed Mar. 28, 2011, the contents of all of which are incorporated herein by reference in their entirety.

TECHNICAL FIELD

The present invention relates to a plant variant lacking a given gene function, a method for producing such plant variant, and a method for accumulating a soluble sugar that regulates the amount of soluble sugar contained in a plant lacking a given gene function.

BACKGROUND ART

ADP-glucose pyrophosphorylase (hereafter, referred to as "AGPase") is a heterotetramer comprising large subunits and small subunits encoded by different genes, and it is an enzyme associated with the starch synthesis pathway. Corn with lowered AGPase activity has heretofore been used for sweet corn breeding and its high sucrose content in seeds (albumens) has been known (Non-Patent Document 1). Also, Patent Document 1 discloses a method for increasing the seed yield of corn by inducing AGPase to express in a stage- or site-specific manner.

Non-Patent Document 2 discloses that inhibition of AGPaseB gene expression via RNAi in potato results in decreased starch content in the tuberous root and in increased sucrose content to a level approximately 10 times greater than that of a wild-type plant. Further, Patent Document 2 discloses that inhibition of AGPase activity in garden pea results in increased sucrose content in beans. Regarding garden pea, Non-Patent Document 3 also discloses that decreased starch content and increased sucrose content were observed in mutant garden pea germs exhibiting approximately 3% to 5% AGPase activity.

Further, Non-Patent Documents 4 and 5 each disclose the correlation between decreased starch content and lack of AGPase activity in *Arabidopsis thaliana*.

Furthermore, Non-Patent Document 6 discloses the floury 2 mutant that affects expression of a plurality of enzymes associated with starch biosynthesis, such as DBE or AGPase, in rice. Regarding rice-derived AGPase, four types of genes (i.e., AGPL1, AGPL2, AGPL3, and AGPL4 genes) are known as genes encoding large subunits, and two types of genes (i.e., AGPS1 and AGPS2 genes) and two types of AGPS2 gene transcription products (i.e., AGPS2a and AGPS2b) are known as genes encoding small subunits. Non-Patent Document 7 discloses that the seed amount is increased in rice into which *E. coli*-derived mutant AGPase (Pi-insensitive or constitutively active) has been introduced.

As disclosed in Patent Documents 3 and 4, regarding modification of AGPase activity, it is known that introduction of site-directed mutation into the AGPS gene encoding the small subunit results in attenuated sensitivity to inorganic phosphate (Pi) and increased seed weight or amount. Thus, the AGPase activity of a plant was known to influence traits such as seed weight or amount.

CITATION LIST

Patent Literature

{PTL 1}
U.S. Pat. No. 7,193,130
{PTL 2}
U.S. Pat. No. 5,498,831
{PTL 3}
EP 1461431
{PTL 4}
US 2003/0177533

Non Patent Literature

{NPL 1}
K. Lertrat, Int. J. Plant Breed., 2007, 1 (1), 27-30
{NPL 2}
B. Muller-Rober, EMBO J., 1992, 11: 1229-1238
{NPL 3}
A. M. Smith., Plant Phys., 1989, 89 (4), 1279-1284
{NPL 4}
T. P. Lin, Plant Phys., 1988, 86, 1175-1181
{NPL 5}
T. P. Lin, Plant Phys., 1988, 86, 1131-1135
{NPL 6}
H. Satoh, Journal of Applied Glycoscience, 2003, 50, 225-230
{NPL 7}
Yasuko S., Nagai, Plant Cell Phys., 2009, 50, 635-643

SUMMARY OF INVENTION

Technical Problem

No techniques that regulate content of a soluble sugar such as sucrose in plant tissue other than seeds were known. Accordingly, it is an object of the present invention to provide a technique that enables production of plants capable of accumulating large quantities of soluble sugars in plant stems and having high soluble sugar content.

Solution to Problem

The present inventors have conducted concentrated studies in order to attain the above object. As a result, they discovered that suppression of a given AGPase gene in a plant enables accumulation of large quantities of soluble sugars in the stem. This has led to the completion of the present invention.

The present invention includes the following.

(1) A plant variant, in which the gene encoding a subunit having high sequence similarity with the subunit encoded by the AGPL1 gene of rice among subunits constituting ADP-glucose pyrophosphorylase of a plant is modified to be suppressed.

(2) The plant variant according to (1), which is derived from a plant other than rice.

(3) The plant variant according to (1), wherein the AGPL1 gene encodes the AGPase subunit comprising the amino acid sequence as shown in SEQ ID NO: 2.

(4) The plant variant according to (1), wherein the plant is a monocotyledonous plant.

(5) The plant variant according to (1), wherein the soluble sugar content in an organ that accumulates excess substances resulting from photosynthesis is significantly higher than the content thereof before modification.

(6) A method for producing a plant variant comprising a step of modification to suppress the gene encoding a subunit having high sequence similarity with the subunit encoded by the AGPL1 gene of rice among subunits constituting ADP-glucose pyrophosphorylase of a plant.

(7) The method for producing a plant variant according to (6), wherein the plant is derived from a plant other than rice.

(8) The method for producing a plant variant according to (6), wherein the AGPL1 gene encodes the AGPase subunit comprising the amino acid sequence as shown in SEQ ID NO: 2.

(9) The method for producing a plant variant according to (6), wherein the plant is a monocotyledonous plant.

(10) The method for producing a plant variant according to (6), wherein the soluble sugar content in an organ that accumulates excess substances resulting from photosynthesis is significantly higher than the content thereof before modification.

(11) The method for producing a plant variant according to (6), which further comprises steps of cultivating the progeny plant after modification and selecting a line with a fixed trait that enables accumulation of large quantities of soluble sugars.

(12) A method for accumulating soluble sugars comprising preparing a plant variant modified so as to suppress the gene encoding a subunit having high sequence similarity with the subunit encoded by the AGPL1 gene of rice among subunits constituting ADP-glucose pyrophosphorylase of a plant and growing the plant variant under conditions that allow photosynthesis.

(13) The method for accumulating soluble sugars according to (12), wherein the plant is derived from a plant other than rice.

(14) The method for accumulating soluble sugars according to (12), wherein the AGPL1 gene encodes the AGPase subunit comprising the amino acid sequence as shown in SEQ ID NO: 2.

(15) The method for accumulating soluble sugars according to (12), wherein the plant is a monocotyledonous plant.

(16) The method for accumulating soluble sugars according to (12), wherein the soluble sugar content in an organ that accumulates excess substances resulting from photosynthesis is significantly higher than the content thereof before modification.

(17) The method for accumulating soluble sugars according to (12), which further comprises steps of cultivating the progeny plant after modification and selecting a line with a fixed trait that enables accumulation of large quantities of soluble sugars.

Advantageous Effects of Invention

According to the present invention, large quantities of soluble sugars can be accumulated in a plant stem by suppressing a given gene, and a plant with high soluble sugar content can be produced. A plant produced in accordance with the present invention contains large quantities of soluble sugars and it thus can be used as a starting material for biofuels.

DESCRIPTION OF EMBODIMENTS

Hereafter, the method for producing a plant containing large quantities of soluble sugars according to the present invention is described in detail.

According to the present invention, a gene encoding a subunit exhibiting the highest sequence similarity with the subunit encoded by the AGPL1 gene of rice among subunits constituting ADP-glucose pyrophosphorylase (AGPase) of a plant is suppressed, in order to accumulate large quantities of soluble sugars in a plant. The term "soluble sugars" used herein collectively refers to sugars dissolved in water, such as sucrose, glucose, and fructose. Accordingly, the expression "large quantities of soluble sugars are accumulated" refers to a case in which large quantities of any one of or a plurality of sugar components (i.e., sucrose, glucose, and fructose) are accumulated. The expression "large quantities of . . . accumulated" refers to a situation in which the amount of soluble sugars accumulated in a plant before the target gene is suppressed is increased to a significant level after the target gene has been suppressed.

In the present invention, "suppression of a gene" refers to disruption of the gene of interest, suppression or lowering of the expression level of such gene, and inhibition of functions of a protein encoded by such gene. The term "disruption of the gene" refers to deletion of a region comprising part of or the entire coding region of the gene from the chromosome and disruption of the gene via introduction of a transposon or the like into the coding region of the gene. A method for lowering the gene expression level is not particularly limited. Examples thereof include a method in which the expression-regulated region of the gene is modified so as to reduce the extent of transcription and a method in which a transcription product of the gene is selectively degraded.

Examples of gene suppression techniques that can be employed in the present invention include the so-called transposon method, the transgene method, the post-transcriptional gene silencing method, the RNAi technique, the nonsense-mediated decay (NMD) method, the libozyme method, the anti-sense method, the miRNA (micro-RNA) method, and the siRNA (small interfering RNA) method.

The gene to be suppressed in the present invention is a gene encoding a subunit exhibiting the highest sequence similarity with the subunit encoded by the AGPL1 gene of rice (it may be referred to as "Os05g0580000") among subunits constituting ADP-glucose pyrophosphorylase. When a plurality of isomers are identified as subunits constituting AGPase in a given plant, specifically, the plant genome is modified so as to suppress the gene encoding a subunit exhibiting the highest sequence similarity with the subunit encoded by the AGPL1 gene of rice. SEQ ID NOs: 1 and 2 show the nucleotide sequence of the AGPL1 gene of rice and the amino acid sequence of the subunit encoded by the AGPL1 gene, respectively. "Sequence similarity" is a value that quantifies the similarity between two amino acid sequences, and it is determined with the use of sequence similarity search software, such as BLAST, PSI-BLAST, or HMMER, under default settings. The gene to be suppressed in the present invention can be a gene having an amino acid sequence having 70% or higher, preferably 80% or higher, more preferably 90% or higher, and most preferably 95% or higher similarity with the amino acid sequence as shown in SEQ ID NO: 2 and encoding a subunit of AGPase. Here, the value of similarity is determined with the use of a database storing a computer program and gene sequence information provided with the BLAST (Basic Local Alignment Search Tool) program under default settings. In other words, the term "the gene to be suppressed in the present invention" is synonymous with the homologous gene of the AGPL1 gene of rice, provided that the plant of such gene is not rice. Homologous genes originating from organisms other than rice are not particularly limited, and such genes can be identified by searching a database storing sequence information of various organism species. Specifically, the nucleotide sequence and the amino acid sequence as shown in SEQ ID NOs: 1 and 2 may be employed as query sequences to search, for example, the international nucleotide sequence database (e.g., DDBJ/EMBL/GenBank) or the SWISS-PROT database. Thus, the gene of interest can be easily searched for and identified from known databases.

The term "homologous genes" generally refers to genes that have evolved and diverged from a common ancestral gene, and the term also refers to homologous genes developed between two species (i.e., orthologs) and homologous genes developed within a single species via duplicate branching (i.e., paralogs). In other words, homologous genes, such as orthologs and paralogs, are within the scope of the "homologous genes" described above.

When a gene of a given plant is modified so as to accumulate large quantities of soluble sugars in which the genomic information of the plant of interest is not known, a genome library or cDNA library may be prepared in accordance with a conventional technique, and hybridization may be carried out using the entire or part of the AGPL1 gene of rice as a probe. Thus, the gene to be suppressed can be identified.

When a plant that is modified so as to accumulate large quantities of soluble sugars is rice, the AGPL1 gene is to be suppressed. Four types of genes; i.e., AGPL1, AGPL2, AGPL3, and AGPL4 genes, are known as subunits constituting rice AGPase. Traits are changed to accumulate large quantities of soluble sugars via suppression of the AGPL1 gene among such genes; however, such trait change cannot be observed when a gene of a different type is suppressed. As described in the examples below, a plant variant resulting from AGPL3 gene suppression accumulated soluble sugars in an amount substantially the same as that in a wild-type plant. SEQ ID NOs: 3 and 4 show the nucleotide sequence of the AGPL3 gene and the amino acid sequence of a subunit encoded by the AGPL3 gene, respectively.

Based on the findings described above, it is preferable to identify a gene exhibiting higher sequence similarity with the nucleotide sequence and the amino acid sequence of the AGPL1 gene as shown in SEQ ID NOs: 1 and 2 than with the nucleotide sequence and the amino acid sequence of the AGPL3 gene as shown in SEQ ID NOs: 3 and 4, when a plant other than rice is modified so as to accumulate large quantities of soluble sugars. As is apparent from the examples below, suppression of a gene exhibiting comparatively higher sequence similarity with the nucleotide sequence and the amino acid sequence of the AGPL1 gene enables production of a plant variant capable of accumulating large quantities of soluble sugars.

Any plants may be modified to accumulate large quantities of soluble sugars without particular limitation. Examples of target plants include, but are not limited to, dicotyledonous plants and monocotyledonous plants, such as plants belonging to Brassicaceae, Gramineae, Solanaceae, Leguminosae, and Salicaceae (see the examples below).

Brassicaceae: *Arabidopsis thaliana, Brassica rapa, Brassica napus, Brassica oleracea* var. *capitata, Brassica rapa, Brassica napus, Brassica rapa* var. *chinensis, Brassica rapa* var. *rapa, Brassica rapa* var. *hakabura, Brassica rapa* var. *lancinifolia, Brassica rapa* var. *peruviridis, Brassica rapa* var. *chinensis, Brassica raphanus sativus, Wasabia japonica*, etc.

Solanaceae: *Nicotiana tabacum, Solanum melongena, Solaneum tuberosum, Lycopersicon lycopersicum, Capsicum annuum, Petunia*, etc.

Leguminosae: *Glycine max, Pisum sativum, Vicia faba, Wisteria floribunda, Arachis. hypogaea, Lotus corniculatus* var. *japonicus, Phaseolus vulgaris, Vigna angularis, Acacia*, etc.

Compositae: *Chrysanthemum morifolium, Helianthus annuus*, etc.

Palmae: *Elaeis guineensis, Elaeis oleifera, Cocos nucifera, Phoenix dactylifera, Copernicia*, etc.

Anacardiaceae: *Rhus succedanea, Anacardium occidentale, Toxicodendron vernicifluum, Mangifera indica, Pistacia vera*, etc.

Cucurbitaceae: *Cucurbita maxima, Cucurbita moschata, Cucurbita pepo, Cucumis sativus, Trichosanthes cucumeroides, Lagenaria siceraria* var. *gourda*, etc.

Rosaceae: *Amygdalus communis, Rosa, Fragaria, Prunus, Malus pumila* var. *domestica*, etc.

Caryophyllaceae: *Dianthus caryophyllus*, etc.

Salicaceae: *Populus trichocarpa, Populus nigra, Populus tremula*, etc.

Myrtaceae: *Eucalyptus camaldulensis, Eucalyptus grandis*, etc.

Gramineae: *Zea mays, Oryza sativa, Hordeum vulgare, Triticum aestivum, Phyllostachys, Saccharum officinarum, Pennisetum pupureum, Erianthus ravenae, Miscanthus virgatum, Sorghum, Panicum*, etc.

Liliaceae: *Tulipa, Lilium*, etc.

Production of monocotyledonous plants capable of accumulating large quantities of soluble sugars is particularly preferable. Among monocotyledonous plants, plants of Gramineae, such as rice, wheat, barley, sugar cane, and corn, are particularly preferable. In particular, plants resulting from suppression of a given gene according to the present invention exhibit traits that enable accumulation of larger quantities of soluble sugars compared with original plants without suppression of the gene. In general, excess sugar components (soluble sugars) photosynthesized in leaves are translocated to an organ that accumulates excess substances resulting from photosynthesis, such as a stem, and they are accumulated therein. Thus, plants resulting from suppression of a given gene according to the present invention exhibit traits that enable accumulation of large quantities of soluble sugars in an organ that accumulates excess substances resulting from photosynthesis, such as a stem. In the case of rice, the leaf sheath and the culm (stem) function as organs that accumulate excess substances resulting from photosynthesis. Specifically, large quantities of soluble sugars are accumulated in the leaf sheath and the culm (stem) in the case of rice.

According to the production method of the present invention, accordingly, plants capable of accumulating large quantities of soluble sugars can be produced. Since such plants have accumulated large quantities of soluble sugars, such plants can be effectively used as starting materials for biofuels. Specifically, the plants produced according to the present invention have accumulated large quantities of soluble sugars and thus can be used for production of biofuels utilizing microorganisms.

In the past, it was difficult to evaluate changes in the accumulation of sucrose in the organs of model plants such as *Arabidopsis thaliana* and rice as described above, because such plants accumulate fats or starch. Since the plants produced according to the present invention accumulate large quantities of soluble sugars in organs such as stems or leaf sheaths, the amount of soluble sugars contained in such organs may be used as an indicator to screen for plants producing increased amounts of soluble sugars, such as sucrose, or causal genes used for production of increased amounts of soluble sugars.

In addition, livestock animals have heretofore been raised with the use of fermented roughage utilizing rice straw or the like. In general, fermented roughage is prepared by adding a sugar component to a plant (e.g., rice straw) to perform lactic acid fermentation with the aid of lactic bacteria. When the plants produced in accordance with the present invention are used as starting materials for fermented roughage, addition of a sugar component for lactic acid fermentation becomes unnecessary because such plants have accumulated large quantities of soluble sugars, as described above. With the utilization of the plants produced in accordance with the present invention, inexpensive and highly nutritional fermented roughage for livestock animals can be produced.

When soluble sugars accumulated in organs that accumulate excess substances resulting from photosynthesis, such as leaf sheaths and stems, are used, it is preferable that plants be used before ear emergence. This is because soluble sugars accumulated in organs that accumulate excess substances resulting from photosynthesis are translocated to the ears in the form of sucrose in plants after ear emergence.

Other Steps

As described above, plants may be modified so as to suppress a given gene, and progeny plants can then be obtained in accordance with a conventional technique. That is, progeny plants sustaining fixed traits that allow accumulation of large quantities of soluble sugars acquired via modification of plants so as to suppress a given gene can be obtained in accordance with a conventional technique.

In the present invention, the term "plant body" refers to a grown individual plant, plant cell, plant tissue, callus, or seed. That is, a substance that can be grown to result in an individual plant in the end is regarded as a plant body in the present invention. Plant cells may be in various forms. Examples of plant cells include suspension cultured cells, protoplasts, and leaf slices. Plant bodies can be obtained by multiplying and differentiating such plant cells. Plant bodies can be reproduced from plant cells via a conventional technique in accordance with plant cell type.

EXAMPLES

Hereafter, the present invention is described in greater detail with reference to the examples, although the technical scope of the present invention is not limited to the examples below.

In this example, the capacity of variants resulting from disruption of subunits constituting rice AGPase to accumulate soluble sugars was examined using a rice model. In this example, variants resulting from disruption of subunits encoded by the AGPL1 gene and variants resulting from disruption of subunits encoded by the AGPL3 gene among subunits constituting rice AGPase were obtained. These variants were provided by the National Institute of Agrobiological Sciences as the collection of Tos17 mutant lines of a rice variety (Nipponbare).

In this example, the two rice seed lines shown below were provided.

TABLE 1

| Tos17 line | Gene | Enzymatic function |
|---|---|---|
| NF3982 | AGPL1 | ADP-Glc Pyrophosphorylase |
| NG7528 | AGPL3 | ADP-Glc Pyrophosphorylase |

Specifically, M1 seeds of the mutant lines (NF3982, NC7528, and NCO371) prepared via translocation of a rice endogenous retrotransposon Tos17 provided by the National Institute of Agrobiological Sciences were cultivated in pots in a greenhouse.

DNA was extracted from leaf blades of seedlings, and genotypes were inspected via PCR to determine whether or not NF3982 lacks AGPL1, NF7528 lacks AGPL3, and NCO371 lacks ISA3.

DNA was extracted in the following manner. At the outset, leaf blades grounded with the use of a Multi-Beads Shocker in an extraction buffer (1 M KCl, 100 mM Tris-HCl (pH 8), 10 mM EDTA) were allowed to stand at 70 degrees C. for 20 minutes or longer. The grounded leaf blades were centrifuged at 15,000 rpm and room temperature for 10 minutes, and 150 microliters of the supernatant was added to the same amount of isopropanol. The resultant was centrifuged at 3,000 rpm and 4 degrees C. for 30 minutes, and a precipitate was obtained. To the precipitate, 200 microliters of 70% ethanol was added, and the resultant was centrifuged at 3,000 rpm and 4 degrees C. for 5 minutes. Thereafter, the supernatant was discarded and the precipitate was air-dried at room temperature for 1 to 2 hours. The air-dried precipitate was dissolved in 1/10 TE and used for PCR.

PCR was carried out using the TaKaRa Multiplex PCR Assay Kit. The reaction was carried out by repeating a cycle of 94 degrees C. for 60 seconds, 94 degrees C. for 30 seconds, 58 degrees C. for 90 seconds, and 72 degrees C. for 90 seconds 35 times, followed by 72 degrees C. for 10 minutes. Primers shown in Table 2 were used, and forward and reverse primers of such lines and the Tos17-tail3 primer were used at the same time.

TABLE 2

| Line or primer name | Forward or Reverse | Sequence | SEQ ID NO: |
|---|---|---|---|
| NF3982 | Forward | CCTCTCTCCAACAGGAGCAC | SEQ ID NO: 5 |
|  | Reverse | ATGATTTGCGTGGTTGTTGA | SEQ ID NO: 6 |
| NG7528 | Forward | TCCATGTAGTCCATGCGGTA | SEQ ID NO: 7 |
|  | Reverse | GCGGTGAGTACAGCGTACAA | SEQ ID NO: 8 |
| NC0371 | Forward | GTTGGTATTTGTCCGAGCGT | SEQ ID NO: 9 |
|  | Reverse | TTCGTCACAGCAACCCAATA | SEQ ID NO: 10 |
| Tos17-tail3 | — | GAGAGCATCATCGGTTACATCTTCTC | SEQ ID NO: 11 |

M2 seeds of WT lines and homozygous KO lines obtained from plants the genotypes of which had been confirmed were seeded, 6 individuals from each line were cultivated in 1/5000-a pots in a greenhouse, and the resultants were subjected to the measurement of sugar and starch concentration and enzyme activity. In the greenhouse, a light period of 14 hours from 5:00 to 19:00 was set, and temperature was set at 27 degrees C. during the light period and 23 degrees C. during the dark period.

Figure 1:
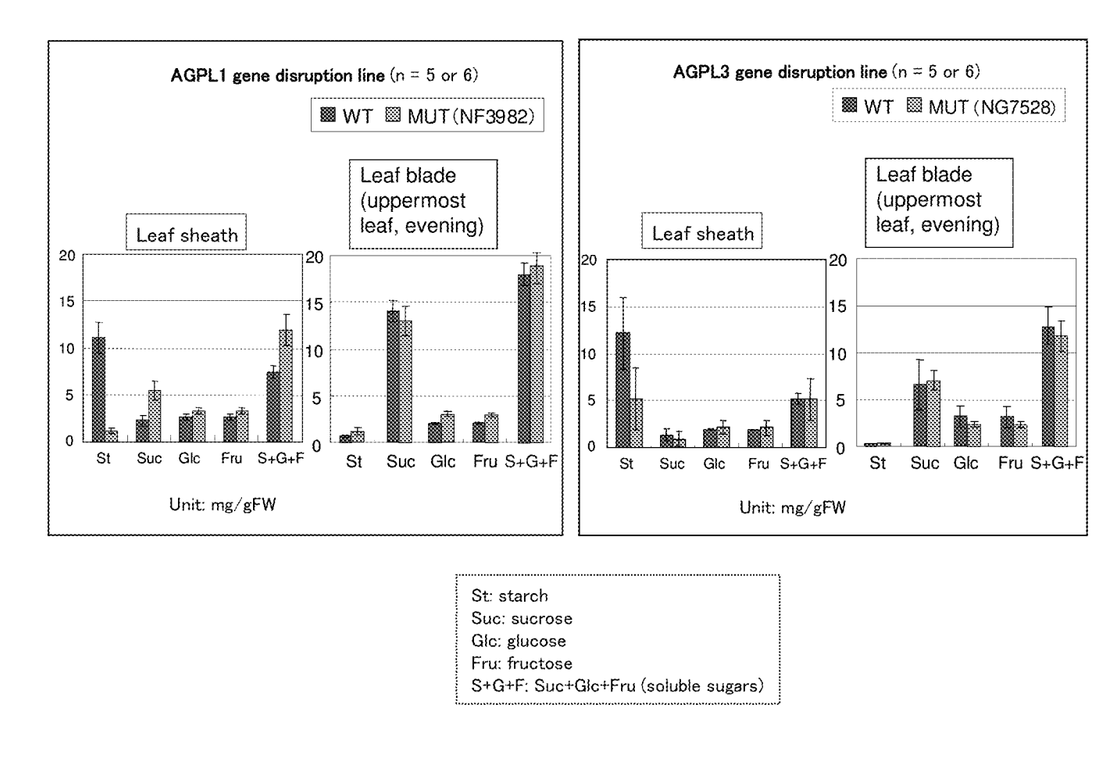
FIG. 1 is a characteristic diagram showing the results of quantification of the amounts of soluble sugars and starch accumulated in the leaf sheaths and in the leaf blades of a variant resulting from AGPL1 gene disruption and of a variant resulting from AGPL3 gene disruption.

Sugar and starch concentration was measured using an F-kit (J. K. International), and measurement was carried out with the use of microplate spectrophotometers (Viento XS, Dainippon Sumitomo Pharma Co., Ltd.). At the outset, 1,000 microliters of 80% ethanol was added to about 50 mg of the test material grounded in liquid nitrogen, and the mixture was thoroughly agitated. Thereafter, the mixture was incubated at 80 degrees C. for 10 minutes, the resultant was centrifuged at 10,000 rpm and room temperature for 5 minutes, and the supernatant was recovered. To the remaining precipitate, 500 microliters of 80% ethanol was added, and the same procedure was carried out. The thus-obtained supernatant was dehydrated with a centrifugal evaporator, 500 microliters of distilled water was added thereto, and the mixture was thoroughly agitated. The resultant was centrifuged at 15,000 rpm and 4 degrees C. for 5 minutes, and the supernatant was recovered as an extract. Concentration of each sugar (mg/ml) in the extract was measured in accordance with the procedure of the F-kit, and sugar concentration per fresh weight was determined based on formula (1).

sugar concentration (mg/gFW)=sugar concentration (mg/ml)×0.5 (ml)/fresh weight (g)   Formula (1):

The results of quantitative analysis of sugar and starch concentration are shown in FIG. 1. In FIG. 1, the term "AGPL1 gene disruption line" refers to a variant of the NF3982 line, and the term "AGPL3 gene disruption line" refers to a variant of the NG7528 line. In FIG. 1, "St" indicates starch, "Suc" indicates sucrose, "Glc" indicates glucose, "Fru" indicates fructose, and "S+G+F" indicates a total of sucrose, glucose, and fructose (i.e., soluble sugars).

The results shown in FIG. 1 demonstrate that the amount of sucrose accumulated in the leaf sheath of a variant resulting from AGPL1 gene disruption increased to a level 2.4 times greater than that in a wild-type line, and the amount of soluble sugars accumulated in the leaf sheath thereof was significantly increased, compared with that in a wild-type line. In addition, the amount of starch accumulated in the leaf sheath of a variant resulting from AGPL1 gene disruption was significantly decreased, compared with that in a wild-type line. In contrast, the amount of soluble sugars such as sucrose, and starch accumulated in the leaf blade of a variant resulting from AGPL1 gene disruption was substantially the same as that in wild-type plants. In addition, the amount of soluble sugars, such as sucrose, and starch accumulated in the leaf sheath and the leaf blade of a variant resulting from AGPL3 gene disruption was substantially the same as that in wild-type plants.

The results demonstrate that disruption of a subunit encoded by the AGPL1 gene among subunits constituting rice AGPase enables accumulation of large quantities of soluble sugars in the leaf sheath.

The invention claimed is:

1. A method for accumulating soluble sugars in leaf sheaths comprising:
   (a) preparing a variant rice plant, said variant rice plant having been modified so as to completely suppress expression of the ADP-Glucose Pyrophosphorylase Large subunit 1 (AGPL1) gene, and wherein said modification increases the accumulation of soluble sugars in the leaf sheaths of said variant rice plant; and
   (b) growing the variant rice plant under conditions that allow photosynthesis, to allow said variant rice plant to accumulate soluble sugars in its leaf sheaths.

2. The method according to claim 1, wherein the AGPL1 gene encodes an AGPase subunit comprising the amino acid sequence of SEQ ID NO: 2.

3. The method according to claim 1, further comprising the steps of:
   (c) cultivating the variant rice plant; and
   (d) producing progeny plants of said variant rice plant, and selecting a progeny plant with a fixed trait of enhanced accumulation of soluble sugars, said progeny plant containing said modification.

* * * * *

SEQUENCE LISTING

<160> NUMBER OF SEQ ID NOS: 11

<210> SEQ ID NO 1
<211> LENGTH: 1560
<212> TYPE: DNA
<213> ORGANISM: Oryza sativa
<220> FEATURE:
<221> NAME/KEY: CDS
<222> LOCATION: (1)..(1560)

<400> SEQUENCE: 1

```
atg cag ttc agc agt gtg ttt ccc tta gag ggt aaa gca tgc gtg agc      48
Met Gln Phe Ser Ser Val Phe Pro Leu Glu Gly Lys Ala Cys Val Ser
1               5                   10                  15 cca ata agg aga ggt ggt gag ggc tca gct agt gat aga ttg aag atc      96
Pro Ile Arg Arg Gly Gly Glu Gly Ser Ala Ser Asp Arg Leu Lys Ile
                20                  25                  30 ggg gac agt agc agc atc aag cat gat aga gca gtg agg agg atg tgt     144
Gly Asp Ser Ser Ser Ile Lys His Asp Arg Ala Val Arg Arg Met Cys
            35                  40                  45 ctt ggt tat agg ggc acc aaa aac ggt gca caa tgt gtg ctc acc tca     192
Leu Gly Tyr Arg Gly Thr Lys Asn Gly Ala Gln Cys Val Leu Thr Ser
        50                  55                  60 gat gct ggc cca gac act ctt cat gtc cga aca tca ttc cgg agg aac     240
Asp Ala Gly Pro Asp Thr Leu His Val Arg Thr Ser Phe Arg Arg Asn
65                  70                  75                  80 ttt gcg gat cca aat gag gtt gct gct gtt ata ttg ggt ggt ggc acc     288
Phe Ala Asp Pro Asn Glu Val Ala Ala Val Ile Leu Gly Gly Gly Thr
                85                  90                  95 ggg act caa ctt ttt cct ctc aca agc aca agg gcc acg cct gct gtt     336
Gly Thr Gln Leu Phe Pro Leu Thr Ser Thr Arg Ala Thr Pro Ala Val
                100                 105                 110 cct att gga gga tgc tat agg ctt atc gat atc ccc atg agc aac tgt     384
```

```
Pro Ile Gly Gly Cys Tyr Arg Leu Ile Asp Ile Pro Met Ser Asn Cys
            115                 120                 125 ttc aac agt ggc ata aac aag ata ttc ata atg act caa ttc aac tca      432
Phe Asn Ser Gly Ile Asn Lys Ile Phe Ile Met Thr Gln Phe Asn Ser
        130                 135                 140 gca tct ctt aat cgt cac att cat cgt acg tac ctt ggt ggt gga atc      480
Ala Ser Leu Asn Arg His Ile His Arg Thr Tyr Leu Gly Gly Gly Ile
145                 150                 155                 160 aac ttt act gat gga tct gtt gag gta tta gcc gct aca caa atg cct      528
Asn Phe Thr Asp Gly Ser Val Glu Val Leu Ala Ala Thr Gln Met Pro
                    165                 170                 175 ggg gag gct gct ggt tgg ttc cag ggt aca gca gat gca gtt aga aaa      576
Gly Glu Ala Ala Gly Trp Phe Gln Gly Thr Ala Asp Ala Val Arg Lys
            180                 185                 190 ttt atc tgg gtt ctt gag gac tat tac aag cat aaa gct ata gaa cac      624
Phe Ile Trp Val Leu Glu Asp Tyr Tyr Lys His Lys Ala Ile Glu His
        195                 200                 205 att tta atc ttg tca gga gat cag ctt tat cgt atg gac tac atg gag      672
Ile Leu Ile Leu Ser Gly Asp Gln Leu Tyr Arg Met Asp Tyr Met Glu
210                 215                 220 ctt gtg cag aaa cat gtt gat gac aat gct gac att act tta tca tgt      720
Leu Val Gln Lys His Val Asp Asp Asn Ala Asp Ile Thr Leu Ser Cys
225                 230                 235                 240 gct cct gtt gga gag agt cga gca tct gac tat gga cta gtg aag ttc      768
Ala Pro Val Gly Glu Ser Arg Ala Ser Asp Tyr Gly Leu Val Lys Phe
                    245                 250                 255 gac agt tca ggc cgt gta att caa ttt tct gaa aaa ccc aag ggc act      816
Asp Ser Ser Gly Arg Val Ile Gln Phe Ser Glu Lys Pro Lys Gly Thr
            260                 265                 270 gac ttg gaa gca atg aaa gtg gat acc agc ttt ctc aat ttt gcc ata      864
Asp Leu Glu Ala Met Lys Val Asp Thr Ser Phe Leu Asn Phe Ala Ile
        275                 280                 285 gac gac ccg act aaa ttt ccc tac att gct tcg atg gga gtt tat gtc      912
Asp Asp Pro Thr Lys Phe Pro Tyr Ile Ala Ser Met Gly Val Tyr Val
290                 295                 300 ttc aaa aga gat gtt ctt tta aac ctt cta aag tca aga tat gca gaa      960
Phe Lys Arg Asp Val Leu Leu Asn Leu Leu Lys Ser Arg Tyr Ala Glu
305                 310                 315                 320 cta cat gac ttt ggg tct gaa atc ctc cca aga gct tta cat gag cac     1008
Leu His Asp Phe Gly Ser Glu Ile Leu Pro Arg Ala Leu His Glu His
                    325                 330                 335 aat gta cag gca tat gtc ttc gct gac tac tgg gaa gac att gga acg     1056
Asn Val Gln Ala Tyr Val Phe Ala Asp Tyr Trp Glu Asp Ile Gly Thr
            340                 345                 350 atc aga tcg ttc ttt gat gca aac atg gcc ctt tgc gag cag cct ccc     1104
Ile Arg Ser Phe Phe Asp Ala Asn Met Ala Leu Cys Glu Gln Pro Pro
        355                 360                 365 aag ttt gag ttt tat gat cca aaa act ccc ttc ttc act tca cct cga     1152
Lys Phe Glu Phe Tyr Asp Pro Lys Thr Pro Phe Phe Thr Ser Pro Arg
370                 375                 380 tat ttg ccg cca aca aag tca gat aaa tgc agg att aaa gat gcg ata     1200
Tyr Leu Pro Pro Thr Lys Ser Asp Lys Cys Arg Ile Lys Asp Ala Ile
385                 390                 395                 400 att tcc cat ggc tgt ttc ttg cgt gaa tgt acc atc gag cat tcg ata     1248
Ile Ser His Gly Cys Phe Leu Arg Glu Cys Thr Ile Glu His Ser Ile
                    405                 410                 415 gtt gga gtc cgc tca cgc ctt aac tct gca tgt gag ctc aag aat acc     1296
Val Gly Val Arg Ser Arg Leu Asn Ser Ala Cys Glu Leu Lys Asn Thr
            420                 425                 430
```

| | | | | | | | | | | | | | | | | |
|---|---|---|---|---|---|---|---|---|---|---|---|---|---|---|---|---|
| atg | atg | atg | ggt | gcg | gat | ttg | tac | gaa | act | gaa | gat | gaa | att | tca | aga | 1344 |
| Met | Met | Met | Gly | Ala | Asp | Leu | Tyr | Glu | Thr | Glu | Asp | Glu | Ile | Ser | Arg | |
| | | 435 | | | | 440 | | | | | 445 | | | | | |
| cta | ctg | tca | gaa | ggc | aag | gtc | ccc | att | ggt | gta | ggg | gaa | aac | aca | aag | 1392 |
| Leu | Leu | Ser | Glu | Gly | Lys | Val | Pro | Ile | Gly | Val | Gly | Glu | Asn | Thr | Lys | |
| | 450 | | | | | 455 | | | | | 460 | | | | | |
| ata | aac | aac | tgc | atc | atc | gac | atg | aac | gcg | agg | gtt | gga | agg | aac | gtg | 1440 |
| Ile | Asn | Asn | Cys | Ile | Ile | Asp | Met | Asn | Ala | Arg | Val | Gly | Arg | Asn | Val | |
| 465 | | | | | 470 | | | | | 475 | | | | | 480 | |
| gtc | atc | aca | aac | agc | gag | ggt | gtc | caa | gaa | agt | gat | cgg | cct | gag | gaa | 1488 |
| Val | Ile | Thr | Asn | Ser | Glu | Gly | Val | Gln | Glu | Ser | Asp | Arg | Pro | Glu | Glu | |
| | | | | 485 | | | | | 490 | | | | | 495 | | |
| ggg | tac | tac | ata | agg | tcg | gga | atc | gtg | gtg | atc | ctg | aag | aac | gcg | acc | 1536 |
| Gly | Tyr | Tyr | Ile | Arg | Ser | Gly | Ile | Val | Val | Ile | Leu | Lys | Asn | Ala | Thr | |
| | | | 500 | | | | | 505 | | | | | 510 | | | |
| atc | aag | gac | ggg | aag | gtc | ata | tag | | | | | | | | | 1560 |
| Ile | Lys | Asp | Gly | Lys | Val | Ile | | | | | | | | | | |
| | | 515 | | | | | | | | | | | | | | |

<210> SEQ ID NO 2
<211> LENGTH: 519
<212> TYPE: PRT
<213> ORGANISM: Oryza sativa

<400> SEQUENCE: 2

| Met | Gln | Phe | Ser | Ser | Val | Phe | Pro | Leu | Glu | Gly | Lys | Ala | Cys | Val | Ser |
|---|---|---|---|---|---|---|---|---|---|---|---|---|---|---|---|
| 1 | | | | 5 | | | | | 10 | | | | | 15 | |

| Pro | Ile | Arg | Arg | Gly | Glu | Gly | Ser | Ala | Ser | Asp | Arg | Leu | Lys | Ile |
|---|---|---|---|---|---|---|---|---|---|---|---|---|---|---|
| | | | 20 | | | | | 25 | | | | | 30 | |

| Gly | Asp | Ser | Ser | Ser | Ile | Lys | His | Asp | Arg | Ala | Val | Arg | Met | Cys |
|---|---|---|---|---|---|---|---|---|---|---|---|---|---|---|
| | | 35 | | | | | 40 | | | | | 45 | | |

| Leu | Gly | Tyr | Arg | Gly | Thr | Lys | Asn | Gly | Ala | Gln | Cys | Val | Leu | Thr | Ser |
|---|---|---|---|---|---|---|---|---|---|---|---|---|---|---|---|
| | 50 | | | | | 55 | | | | | 60 | | | | |

| Asp | Ala | Gly | Pro | Asp | Thr | Leu | His | Val | Arg | Thr | Ser | Phe | Arg | Arg | Asn |
|---|---|---|---|---|---|---|---|---|---|---|---|---|---|---|---|
| 65 | | | | | 70 | | | | | 75 | | | | | 80 |

| Phe | Ala | Asp | Pro | Asn | Glu | Val | Ala | Ala | Val | Ile | Leu | Gly | Gly | Gly | Thr |
|---|---|---|---|---|---|---|---|---|---|---|---|---|---|---|---|
| | | | | 85 | | | | | 90 | | | | | 95 | |

| Gly | Thr | Gln | Leu | Phe | Pro | Leu | Thr | Ser | Thr | Arg | Ala | Thr | Pro | Ala | Val |
|---|---|---|---|---|---|---|---|---|---|---|---|---|---|---|---|
| | | | 100 | | | | | 105 | | | | | 110 | | |

| Pro | Ile | Gly | Gly | Cys | Tyr | Arg | Leu | Ile | Asp | Ile | Pro | Met | Ser | Asn | Cys |
|---|---|---|---|---|---|---|---|---|---|---|---|---|---|---|---|
| | | 115 | | | | | 120 | | | | | 125 | | | |

| Phe | Asn | Ser | Gly | Ile | Asn | Lys | Ile | Phe | Ile | Met | Thr | Gln | Phe | Asn | Ser |
|---|---|---|---|---|---|---|---|---|---|---|---|---|---|---|---|
| | 130 | | | | | 135 | | | | | 140 | | | | |

| Ala | Ser | Leu | Asn | Arg | His | Ile | His | Arg | Thr | Tyr | Leu | Gly | Gly | Gly | Ile |
|---|---|---|---|---|---|---|---|---|---|---|---|---|---|---|---|
| 145 | | | | | 150 | | | | | 155 | | | | | 160 |

| Asn | Phe | Thr | Asp | Gly | Ser | Val | Glu | Val | Leu | Ala | Ala | Thr | Gln | Met | Pro |
|---|---|---|---|---|---|---|---|---|---|---|---|---|---|---|---|
| | | | | 165 | | | | | 170 | | | | | 175 | |

| Gly | Glu | Ala | Ala | Gly | Trp | Phe | Gln | Gly | Thr | Ala | Asp | Ala | Val | Arg | Lys |
|---|---|---|---|---|---|---|---|---|---|---|---|---|---|---|---|
| | | | 180 | | | | | 185 | | | | | 190 | | |

| Phe | Ile | Trp | Val | Leu | Glu | Asp | Tyr | Tyr | Lys | His | Lys | Ala | Ile | Glu | His |
|---|---|---|---|---|---|---|---|---|---|---|---|---|---|---|---|
| | | 195 | | | | | 200 | | | | | 205 | | | |

| Ile | Leu | Ile | Leu | Ser | Gly | Asp | Gln | Leu | Tyr | Arg | Met | Asp | Tyr | Met | Glu |
|---|---|---|---|---|---|---|---|---|---|---|---|---|---|---|---|
| | 210 | | | | | 215 | | | | | 220 | | | | |

| Leu | Val | Gln | Lys | His | Val | Asp | Asp | Asn | Ala | Asp | Ile | Thr | Leu | Ser | Cys |
|---|---|---|---|---|---|---|---|---|---|---|---|---|---|---|---|
| 225 | | | | | 230 | | | | | 235 | | | | | 240 |

| Ala | Pro | Val | Gly | Glu | Ser | Arg | Ala | Ser | Asp | Tyr | Gly | Leu | Val | Lys | Phe |
|---|---|---|---|---|---|---|---|---|---|---|---|---|---|---|---|
| | | | | 245 | | | | | 250 | | | | | 255 | |

```
                -continued

Asp Ser Ser Gly Arg Val Ile Gln Phe Ser Glu Lys Pro Lys Gly Thr
            260                 265                 270

Asp Leu Glu Ala Met Lys Val Asp Thr Ser Phe Leu Asn Phe Ala Ile
        275                 280                 285

Asp Asp Pro Thr Lys Phe Pro Tyr Ile Ala Ser Met Gly Val Tyr Val
    290                 295                 300

Phe Lys Arg Asp Val Leu Leu Asn Leu Leu Lys Ser Arg Tyr Ala Glu
305                 310                 315                 320

Leu His Asp Phe Gly Ser Glu Ile Leu Pro Arg Ala Leu His Glu His
                325                 330                 335

Asn Val Gln Ala Tyr Val Phe Ala Asp Tyr Trp Glu Asp Ile Gly Thr
            340                 345                 350

Ile Arg Ser Phe Phe Asp Ala Asn Met Ala Leu Cys Glu Gln Pro Pro
        355                 360                 365

Lys Phe Glu Phe Tyr Asp Pro Lys Thr Pro Phe Phe Thr Ser Pro Arg
    370                 375                 380

Tyr Leu Pro Pro Thr Lys Ser Asp Lys Cys Arg Ile Lys Asp Ala Ile
385                 390                 395                 400

Ile Ser His Gly Cys Phe Leu Arg Glu Cys Thr Ile Glu His Ser Ile
                405                 410                 415

Val Gly Val Arg Ser Arg Leu Asn Ser Ala Cys Glu Leu Lys Asn Thr
            420                 425                 430

Met Met Met Gly Ala Asp Leu Tyr Glu Thr Glu Asp Glu Ile Ser Arg
        435                 440                 445

Leu Leu Ser Glu Gly Lys Val Pro Ile Gly Val Gly Asn Thr Lys
    450                 455                 460

Ile Asn Asn Cys Ile Ile Asp Met Asn Ala Arg Val Gly Arg Asn Val
465                 470                 475                 480

Val Ile Thr Asn Ser Glu Gly Val Gln Glu Ser Asp Arg Pro Glu Glu
                485                 490                 495

Gly Tyr Tyr Ile Arg Ser Gly Ile Val Val Ile Leu Lys Asn Ala Thr
            500                 505                 510

Ile Lys Asp Gly Lys Val Ile
        515

<210> SEQ ID NO 3
<211> LENGTH: 1536
<212> TYPE: DNA
<213> ORGANISM: Oryza sativa
<220> FEATURE:
<221> NAME/KEY: CDS
<222> LOCATION: (1)..(1536)

<400> SEQUENCE: 3 atg gcg gcg atg gac ctg cgg gtg gcc gcc ccg gcc tcc gtg gcc gcg      48
Met Ala Ala Met Asp Leu Arg Val Ala Ala Pro Ala Ser Val Ala Ala
1               5                   10                  15 gcg gcg cgg tgc ggc acg agc ctg gcg agg ccg tgg cct gcc cgg gcg      96
Ala Ala Arg Cys Gly Thr Ser Leu Ala Arg Pro Trp Pro Ala Arg Ala
            20                  25                  30 gtg gga gga gga gga gga gga gga cgg ggc cgg cgt ctc tcc gtg           144
Val Gly Gly Gly Gly Gly Gly Gly Arg Gly Arg Arg Leu Ser Val
        35                  40                  45 cgg acg tcc gtc gcg acc acc gag gcc gcc gcc gcc gcc gtg ggc gcc      192
Arg Thr Ser Val Ala Thr Thr Glu Ala Ala Ala Ala Ala Val Gly Ala
    50                  55                  60
```

-continued

| | | |
|---|---|---|
| tcg gag gac gcg gcg ctg gag gcg cgg gac tcg aag acg gtg gtg gcg<br>Ser Glu Asp Ala Ala Leu Glu Ala Arg Asp Ser Lys Thr Val Val Ala<br>65                                  70                            75                            80 | 240 | |
| gtc atc ctc ggc ggc ggc gcg ggg acg agg ctg ttc ccg ctc acc aag<br>Val Ile Leu Gly Gly Gly Ala Gly Thr Arg Leu Phe Pro Leu Thr Lys<br>                           85                            90                           95 | 288 | |
| cgc agg gcc aag ccc gcg gtg ccc att ggc gga gcg tac agg ctg atc<br>Arg Arg Ala Lys Pro Ala Val Pro Ile Gly Gly Ala Tyr Arg Leu Ile<br>                          100                           105                          110 | 336 | |
| gac gtg ccg atg agc aac tgc ata aac agc ggc atc aac aag gtg tac<br>Asp Val Pro Met Ser Asn Cys Ile Asn Ser Gly Ile Asn Lys Val Tyr<br>              115                           120                           125 | 384 | |
| att ctc acc cag ttc aac tcc gcg tcg ctc aac cgg cac ctt tcc cgg<br>Ile Leu Thr Gln Phe Asn Ser Ala Ser Leu Asn Arg His Leu Ser Arg<br>130                               135                           140 | 432 | |
| gcg tat aac ttc agc aac ggc gtc gcg ttt gga gat gga ttc gtc gag<br>Ala Tyr Asn Phe Ser Asn Gly Val Ala Phe Gly Asp Gly Phe Val Glu<br>145                               150                           155                          160 | 480 | |
| gtc cta gca gca act cag acg cct gga tcg gag gga aag agg tgg ttt<br>Val Leu Ala Ala Thr Gln Thr Pro Gly Ser Glu Gly Lys Arg Trp Phe<br>                          165                           170                          175 | 528 | |
| cag ggt aca gct gat gct gtt cgg caa ttt gac tgg ctt ttt gat gat<br>Gln Gly Thr Ala Asp Ala Val Arg Gln Phe Asp Trp Leu Phe Asp Asp<br>              180                           185                           190 | 576 | |
| gcc aaa gct aaa gac atc gat gat gtg ctg att ctt tct ggt gat cat<br>Ala Lys Ala Lys Asp Ile Asp Asp Val Leu Ile Leu Ser Gly Asp His<br>                      195                           200                           205 | 624 | |
| ctc tac cgc atg gac tac atg gac ttt gtt cag agt cat cgg caa aga<br>Leu Tyr Arg Met Asp Tyr Met Asp Phe Val Gln Ser His Arg Gln Arg<br>210                               215                           220 | 672 | |
| ggt gca gac atc agc atc tgt tgc ttg cct att gat gat agc cgg gca<br>Gly Ala Asp Ile Ser Ile Cys Cys Leu Pro Ile Asp Asp Ser Arg Ala<br>225                               230                           235                          240 | 720 | |
| tct gat ttt ggt cta atg aag ata gac gac aca gga aga gtt atc gca<br>Ser Asp Phe Gly Leu Met Lys Ile Asp Asp Thr Gly Arg Val Ile Ala<br>                          245                           250                          255 | 768 | |
| ttt agt gaa aaa cca aaa gga gat gat tta aag gca atg caa gtt gac<br>Phe Ser Glu Lys Pro Lys Gly Asp Asp Leu Lys Ala Met Gln Val Asp<br>                    260                           265                           270 | 816 | |
| acc act gtt cta ggc tta cca cag gat gaa gca aag gag aag cca tac<br>Thr Thr Val Leu Gly Leu Pro Gln Asp Glu Ala Lys Glu Lys Pro Tyr<br>                        275                           280                          285 | 864 | |
| ata gcg tca atg ggg gtt tat ata ttt aag aaa gag ata ctt cta aat<br>Ile Ala Ser Met Gly Val Tyr Ile Phe Lys Lys Glu Ile Leu Leu Asn<br>              290                           295                           300 | 912 | |
| ctt ttg aga tgg cgt ttt ccc aca gca aat gac ttt gga tct gaa atc<br>Leu Leu Arg Trp Arg Phe Pro Thr Ala Asn Asp Phe Gly Ser Glu Ile<br>305                               310                           315                          320 | 960 | |
| att cct gct tca gca aaa gaa atc aat gta aag gca tat ctt ttc aat<br>Ile Pro Ala Ser Ala Lys Glu Ile Asn Val Lys Ala Tyr Leu Phe Asn<br>                        325                           330                          335 | 1008 | |
| gat tac tgg gaa gac ata gga act ata aaa tca ttc ttt gaa gcc aat<br>Asp Tyr Trp Glu Asp Ile Gly Thr Ile Lys Ser Phe Phe Glu Ala Asn<br>                    340                           345                           350 | 1056 | |
| ctt tct ctt gct gaa cag cca ccg aga ttc agc ttt tat gat gct aat<br>Leu Ser Leu Ala Glu Gln Pro Pro Arg Phe Ser Phe Tyr Asp Ala Asn<br>                  355                           360                          365 | 1104 | |
| aaa cca atg tac aca tca cgg aga aac tta ccg cca tct atg atc aat<br>Lys Pro Met Tyr Thr Ser Arg Arg Asn Leu Pro Pro Ser Met Ile Asn<br>370                               375                           380 | 1152 | |

```
aat agt aag atc act gat tca atc att tcc cat gga tgt ttc ttg gat      1200
Asn Ser Lys Ile Thr Asp Ser Ile Ile Ser His Gly Cys Phe Leu Asp
385                 390                 395                 400 agc tgc agg ata gag cac agt gtt gtt gga atc cgt tct agg ata ggt      1248
Ser Cys Arg Ile Glu His Ser Val Val Gly Ile Arg Ser Arg Ile Gly
                405                 410                 415 tcc aat gtg cac ctc aag gat aca gta atg ctt ggt gct gat ttc tat      1296
Ser Asn Val His Leu Lys Asp Thr Val Met Leu Gly Ala Asp Phe Tyr
            420                 425                 430 gag act gat ctg gaa aga gga gaa ctg ctg gct gaa gga aag gtt cct      1344
Glu Thr Asp Leu Glu Arg Gly Glu Leu Leu Ala Glu Gly Lys Val Pro
        435                 440                 445 att gga atc ggg gag aat aca aag att cag aac tgc ata ata gac aag      1392
Ile Gly Ile Gly Glu Asn Thr Lys Ile Gln Asn Cys Ile Ile Asp Lys
    450                 455                 460 aat gcg agg ata ggg aag aat gta aca att tcc aac tct gag ggt gta      1440
Asn Ala Arg Ile Gly Lys Asn Val Thr Ile Ser Asn Ser Glu Gly Val
465                 470                 475                 480 cag gaa gca gat agg acc tct gaa ggc ttc tac atc cga tca ggc atc      1488
Gln Glu Ala Asp Arg Thr Ser Glu Gly Phe Tyr Ile Arg Ser Gly Ile
                485                 490                 495 acc atc gta tta aag aac tcg ata att gca gat gga tta gtc atc tga      1536
Thr Ile Val Leu Lys Asn Ser Ile Ile Ala Asp Gly Leu Val Ile
            500                 505                 510

<210> SEQ ID NO 4
<211> LENGTH: 511
<212> TYPE: PRT
<213> ORGANISM: Oryza sativa

<400> SEQUENCE: 4

Met Ala Ala Met Asp Leu Arg Val Ala Ala Pro Ala Ser Val Ala Ala
1               5                   10                  15

Ala Ala Arg Cys Gly Thr Ser Leu Ala Arg Pro Trp Pro Ala Arg Ala
            20                  25                  30

Val Gly Gly Gly Gly Gly Gly Gly Arg Gly Arg Arg Leu Ser Val
        35                  40                  45

Arg Thr Ser Val Ala Thr Thr Glu Ala Ala Ala Ala Val Gly Ala
    50                  55                  60

Ser Glu Asp Ala Ala Leu Glu Ala Arg Asp Ser Lys Thr Val Val Ala
65                  70                  75                  80

Val Ile Leu Gly Gly Gly Ala Gly Thr Arg Leu Phe Pro Leu Thr Lys
                85                  90                  95

Arg Arg Ala Lys Pro Ala Val Pro Ile Gly Gly Ala Tyr Arg Leu Ile
            100                 105                 110

Asp Val Pro Met Ser Asn Cys Ile Asn Ser Gly Ile Asn Lys Val Tyr
        115                 120                 125

Ile Leu Thr Gln Phe Asn Ser Ala Ser Leu Asn Arg His Leu Ser Arg
    130                 135                 140

Ala Tyr Asn Phe Ser Asn Gly Val Ala Phe Gly Asp Gly Phe Val Glu
145                 150                 155                 160

Val Leu Ala Ala Thr Gln Thr Pro Gly Ser Glu Gly Lys Arg Trp Phe
                165                 170                 175

Gln Gly Thr Ala Asp Ala Val Arg Gln Phe Asp Trp Leu Phe Asp Asp
            180                 185                 190

Ala Lys Ala Lys Asp Ile Asp Asp Val Leu Ile Leu Ser Gly Asp His
        195                 200                 205
```

Leu Tyr Arg Met Asp Tyr Met Asp Phe Val Gln Ser His Arg Gln Arg
        210                 215                 220

Gly Ala Asp Ile Ser Ile Cys Cys Leu Pro Ile Asp Asp Ser Arg Ala
225                 230                 235                 240

Ser Asp Phe Gly Leu Met Lys Ile Asp Asp Thr Gly Arg Val Ile Ala
                245                 250                 255

Phe Ser Glu Lys Pro Lys Gly Asp Asp Leu Lys Ala Met Gln Val Asp
                260                 265                 270

Thr Thr Val Leu Gly Leu Pro Gln Asp Glu Ala Lys Glu Lys Pro Tyr
            275                 280                 285

Ile Ala Ser Met Gly Val Tyr Ile Phe Lys Lys Glu Ile Leu Leu Asn
            290                 295                 300

Leu Leu Arg Trp Arg Phe Pro Thr Ala Asn Asp Phe Gly Ser Glu Ile
305                 310                 315                 320

Ile Pro Ala Ser Ala Lys Glu Ile Asn Val Lys Ala Tyr Leu Phe Asn
                325                 330                 335

Asp Tyr Trp Glu Asp Ile Gly Thr Ile Lys Ser Phe Phe Glu Ala Asn
                340                 345                 350

Leu Ser Leu Ala Glu Gln Pro Pro Arg Phe Ser Phe Tyr Asp Ala Asn
            355                 360                 365

Lys Pro Met Tyr Thr Ser Arg Arg Asn Leu Pro Pro Ser Met Ile Asn
            370                 375                 380

Asn Ser Lys Ile Thr Asp Ser Ile Ile Ser His Gly Cys Phe Leu Asp
385                 390                 395                 400

Ser Cys Arg Ile Glu His Ser Val Val Gly Ile Arg Ser Arg Ile Gly
                405                 410                 415

Ser Asn Val His Leu Lys Asp Thr Val Met Leu Gly Ala Asp Phe Tyr
            420                 425                 430

Glu Thr Asp Leu Glu Arg Gly Glu Leu Leu Ala Glu Gly Lys Val Pro
            435                 440                 445

Ile Gly Ile Gly Glu Asn Thr Lys Ile Gln Asn Cys Ile Ile Asp Lys
            450                 455                 460

Asn Ala Arg Ile Gly Lys Asn Val Thr Ile Ser Asn Ser Glu Gly Val
465                 470                 475                 480

Gln Glu Ala Asp Arg Thr Ser Glu Gly Phe Tyr Ile Arg Ser Gly Ile
                485                 490                 495

Thr Ile Val Leu Lys Asn Ser Ile Ile Ala Asp Gly Leu Val Ile
            500                 505                 510

<210> SEQ ID NO 5
<211> LENGTH: 20
<212> TYPE: DNA
<213> ORGANISM: Artificial Sequence
<220> FEATURE:
<223> OTHER INFORMATION: Synthetic DNA

<400> SEQUENCE: 5
cctctctcca acaggagcac                                             20

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA

<400> SEQUENCE: 6

```
atgatttgcg tggttgttga                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic DNA

<400> SEQUENCE: 7
tccatgtagt ccatgcggta                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
gcggtgagta cagcgtacaa                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
gttggtattt gtccgagcgt                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA

<400> SEQUENCE: 10
ttcgtcacag caacccaata                                              20

<210> SEQ ID NO 11
<211> LENGTH: 26
<212> TYPE: DNA
<213> ORGANISM: Artificial Sequence
<220> FEATURE:
<223> OTHER INFORMATION: Synthetic DNA

<400> SEQUENCE: 11
gagagcatca tcggttacat cttctc                                       26
```